US011992593B2

(12) United States Patent
Müller et al.

(10) Patent No.: US 11,992,593 B2
(45) Date of Patent: May 28, 2024

(54) MEDICAL CONDENSATE TRAP FOR MEDICAL USE, METHOD FOR DEHUMIDIFYING, BLOOD TREATMENT APPARATUS, BLOOD TREATMENT DEVICE

(71) Applicant: Fresenius Medical Care Deutschland GmbH, Bad Homburg (DE)

(72) Inventors: Ralf Müller, Bad Homburg (DE); Joachim Noack, Bad Neustadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1126 days.

(21) Appl. No.: 16/302,416

(22) PCT Filed: May 16, 2017

(86) PCT No.: PCT/EP2017/061739
§ 371 (c)(1),
(2) Date: Nov. 16, 2018

(87) PCT Pub. No.: WO2017/198670
PCT Pub. Date: Nov. 23, 2017

(65) Prior Publication Data
US 2019/0275229 A1   Sep. 12, 2019

(30) Foreign Application Priority Data
May 20, 2016  (DE) .......................... 102016109340.8

(51) Int. Cl.
*A61M 1/36* (2006.01)
*A61M 1/14* (2006.01)
(Continued)

(52) U.S. Cl.
CPC ................ *A61M 1/30* (2013.01); *A61M 1/14* (2013.01); *A61M 1/34* (2013.01);
(Continued)

(58) Field of Classification Search
CPC ............ A61M 1/14; A61M 1/30; A61M 1/34; A61M 1/3627; A61M 2205/07;
(Continued)

(56) References Cited

U.S. PATENT DOCUMENTS

| 5,863,421 A | 1/1999 | Peter et al. |
| 2009/0008331 A1* | 1/2009 | Wilt .................... A61M 1/3643 |
| | | 210/321.71 |

(Continued)

FOREIGN PATENT DOCUMENTS

| CN | 1956744 | 5/2007 |
| CN | 101848740 | 9/2010 |

(Continued)

OTHER PUBLICATIONS

'AirLife Respiratory Products', CareFusion (Year: 2012).*
(Continued)

*Primary Examiner* — Benjamin J Klein
(74) *Attorney, Agent, or Firm* — Fish & Richardson P.C.

(57) ABSTRACT

The present disclosure relates to a medical condensate trap for use in external blood treatment by means of a blood treatment apparatus. The condensate trap comprises an interior; a first connection for connecting the interior in fluid communication to a gas outlet of the blood treatment apparatus; a second connection for connecting the interior in fluid communication to a gas inlet of the blood treatment apparatus; and a third connection for connecting the interior to an air port of a blood treatment device. The blood treatment device may be, for example, a blood tubing set or a blood cassette.

13 Claims, 4 Drawing Sheets

(51) Int. Cl.
  *A61M 1/30* (2006.01)
  *A61M 1/34* (2006.01)
(52) U.S. Cl.
  CPC ... *A61M 1/362263* (2022.05); *A61M 2205/07* (2013.01); *A61M 2205/12* (2013.01); *A61M 2205/3606* (2013.01); *A61M 2205/3673* (2013.01); *A61M 2205/7536* (2013.01)
(58) Field of Classification Search
  CPC ...... A61M 2205/12; A61M 2205/3606; A61M 2205/3673; A61M 2205/7536; A61M 1/3638; A61M 2205/3638
  See application file for complete search history.

(56) References Cited

U.S. PATENT DOCUMENTS

| | | | |
|---|---|---|---|
| 2009/0159515 | A1 | 6/2009 | Kim et al. |
| 2010/0101657 | A1* | 4/2010 | Morley ............... B01D 63/16 |
| | | | 137/565.37 |
| 2010/0234787 | A1 | 9/2010 | Masaoka |
| 2010/0292627 | A1* | 11/2010 | Caleffi ............... A61M 1/3627 |
| | | | 210/188 |
| 2011/0077605 | A1 | 3/2011 | Karpowicz et al. |
| 2014/0112828 | A1 | 4/2014 | Grant et al. |
| 2017/0189597 | A1* | 7/2017 | Caluya ................ A61M 1/166 |
| 2017/0326282 | A1* | 11/2017 | Wilt .................... F04B 43/0733 |
| 2018/0200469 | A1* | 7/2018 | Higginbotham .. A61M 16/1075 |

FOREIGN PATENT DOCUMENTS

| | | |
|---|---|---|
| DE | 8700221 | 5/1987 |
| DE | 10224750 | 12/2003 |
| DE | 102009024467 | 12/2010 |
| EP | 2213317 | 8/2010 |
| WO | WO 90/04425 | 5/1990 |

OTHER PUBLICATIONS

CareFusion_Airlife_HPFY (Year: 2023).*
Croser et al., "Compressed air generation and supply," 2003; pp. 129-154; ISBN 978-3-642-58358-2.
International Preliminary Report on Patentability in Application No. PCT/EP2017/061739, dated Nov. 20, 2018, 9 pages (English Translation).
International Search Report and Written Opinion in Application No. PCT/EP2017/061739, dated Aug. 10, 2017, 12 pages (English Translation).

* cited by examiner

MEDICAL CONDENSATE TRAP FOR MEDICAL USE, METHOD FOR DEHUMIDIFYING, BLOOD TREATMENT APPARATUS, BLOOD TREATMENT DEVICE

CROSS-REFERENCE TO RELATED APPLICATIONS

The present application is the national stage entry of International Patent Application No. PCT/EP2017/061739, filed on May 16, 2017, and claims priority to Application No. DE 10 2016 109 340.8, filed in the Federal Republic of Germany on May 20, 2016, the disclosures of which are incorporated herein by reference.

TECHNICAL FIELD

The present disclosure relates to a medical condensate trap, a method, a blood treatment apparatus, and a blood treatment device.

BACKGROUND

Blood treatment apparatuses for the extracorporeal blood treatment of blood are known in the prior art. In these, blood is conveyed through disposables such as blood tubes or blood cassettes (hereinafter in short: treatment devices) prior to being conveyed back into the vascular system of the patient. During the blood treatment, undesired condensation of humidity may take place on the disposables being used or on components of the employed blood treatment apparatus.

SUMMARY

According to the disclosure, a medical condensate trap is thus disclosed for use in external blood treatment by means of a blood treatment apparatus. The condensate trap comprises at least an interior for receiving a gas. It comprises at least a first port which is in fluid communication with the interior and which may serve connecting the interior to e.g. a gas outlet of the blood treatment apparatus.

The condensation trap further comprises at least a second port for connecting the interior in fluid communication, e.g. for connecting to a gas inlet of the blood treatment apparatus.

Finally, the condensate trap comprises at least a third port for connecting the interior in fluid communication, e.g. for connecting to an air port or pneumatic port of a blood treatment device, e.g. of a blood tubing set or of a blood cassette.

In this, the connection may be achieved directly (without using a connecting tube) or indirectly (e.g. using a connecting tube).

The method comprises dehumidifying at least a portion of a blood treatment device and/or a portion of a blood treatment apparatus, e.g. of a single-needle pneumatic unit, of a compressor or sections or components of each, for example pneumatic tubes or compressor sections.

The method encompasses providing a blood treatment apparatus, a condensate trap and a blood treatment device.

The blood treatment apparatus comprises a gas outlet and a gas inlet being embodied separately thereof, which are embodied for example as ports. The blood treatment apparatus further comprises a blood pump and a compressor for generating compressed air. The compressor is in fluid communication with the gas outlet.

The blood treatment device comprises a blood line or blood chamber, an air port and a hydrophobic membrane (denoted also as hydrophobic filter). The air port is arranged in fluid communication with the hydrophobic membrane. The side of the hydrophobic membrane facing the air port is referred to herein as its air port-facing side.

The air port of the blood treatment device is connected to the gas outlet of the blood treatment apparatus. The blood line or the blood chamber are connected to the blood pump.

The blood line or the blood chamber are particularly in fluid communication with the air port as well.

The method encompasses at least a single execution of a de-aeration procedure, which method encompasses the following steps: Optionally: building up, by means of the blood pump and/or by means of the compressor, a pre-determined pressure or minimum pressure within the blood treatment device on the side of the hydrophobic membrane facing away from the air port; releasing the pressure through opening a valve towards the hydrophobic membrane; and optionally: conveying, with an open valve using the compressor, between condensate collection and compressor inlet.

In some embodiments, a blood treatment apparatus comprises, or is connected to, at least one device for separating the condensate.

The blood treatment device can be a blood tubing set, or a part thereof, and/or a blood cassette. It comprises, or is connected to, a condensate trap.

In all of the embodiments, the use of the expression "may be" or "may have" and so on, is to be understood synonymously with "preferably is" or "preferably has," and so on, respectively, and is intended to illustrate an embodiment according to the present disclosure.

Embodiments according to the present disclosure may comprise one or several of the aforementioned or the following features. Embodiments according to the present disclosure are furthermore subject-matter of the dependent claims.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all used numerical words.

The spatial information "top" and "bottom" are to be understood herein, in case of doubt by the person skilled in the art, as absolute or relative spatial information which refer to the arrangement of the concerned or relevant component during its usual use and/or to the illustration as seen in the accompanying figures.

The present disclosure relates to any arbitrary combination of features mentioned herein, unless a certain combination is recognized by the person skilled in the art to be technically impossible.

In some exemplary embodiments, the condensate trap comprises exactly three ports, namely, the first, second and third.

In some exemplary embodiments, the third port is arranged in a use position of the condensate trap, higher than the first port and/or than the second port.

In some exemplary embodiments, the first port is arranged, in a use position of the condensate trap, higher than the second port.

In some exemplary embodiments, the third port is associated with a first end area of the interior or with a first end area of the condensate trap. The second port is associated with a second end area, which is positioned opposite to the first end area, of the interior or of the condensate trap. The first port is arranged between the second port and the third port.

In some exemplary embodiments, the interior, which extends in longitudinal direction and in a transverse direction, is separated from or sealed against the exterior of the condensate trap by means of a housing.

The housing comprises at least a first opening for a gas exchange with the interior through the first port, at least a second opening for a gas exchange with the interior through the second port and at least a third opening for a gas exchange with the interior through the third port.

In some exemplary embodiments, the distance between the first opening and the third opening is equal to at least the extension in transverse section of the interior. Alternatively, it is larger than this extension. The first and the third openings may be interchanged, which is still within the scope of the present invention. Preferably, the opening is disposed above the fluid level.

In some exemplary embodiments, the distance between the first opening and the second opening is at least equal to the extension in transverse direction. Alternatively, it is larger than this extension.

In some exemplary embodiments, the diameter and/or a length of an area of the first opening, the second opening and/or the third opening or the inner diameter of the tubes or connecting lines, which are connected to the ports, is smaller than the extension of the interior in transverse direction. An achievable advantage may be that pushing condensate drops towards the air port or pneumatic port through the thus obtained transverse expansion to the inside may be rendered difficult or may be prevented.

In some exemplary embodiments, the blood treatment apparatus comprises a single-needle tank. The blood treatment device is a blood cassette. The blood line or blood chamber is, or comprises, a single-needle chamber. The hydrophobic membrane is arranged in a fluid communication between the air port and the single-needle chamber. The pre-determined pressure or minimum pressure is built up in the single-needle chamber. The pressure is released towards a single-needle tank of the blood treatment apparatus or into the surroundings. The section of the blood treatment apparatus, in which conveying takes place with an open valve using the compressor, is a section of a single-needle pneumatic unit.

In some exemplary embodiments, the method further encompasses that the de-aeration procedure is executed or started when a pre-determined condition has been fulfilled. This may be, completing a pre-determined period of time since the de-aeration executed last; reaching/falling below a pre-determined temperature, in particular measured with a sensor in the area of the air port or of the pneumatic port; reaching/falling below a predetermines flow ratio measured with a flow sensor of the blood treatment apparatus which may be provided at a suitable site; detecting a pre-determined wavelength in transmissions or scattered light measurements at the gas inlet.

In some exemplary embodiments, the device for separating condensate is, or comprises, a condensate trap.

In some exemplary embodiments, the blood treatment apparatus comprises a gas outlet and a gas inlet being embodied separately therefrom.

In some exemplary embodiments, the blood treatment apparatus comprises a compressor or another device for generating compressed air or a condensate collection. The compressor is connected to the gas outlet. The condensate collection is connected to the gas inlet.

In some exemplary embodiments, the blood treatment apparatus is connected to a blood treatment device, which is embodied as blood tubing set (or part thereof) and/or as blood cassette, each comprising a hydrophobic membrane. The condensate trap is thereby arranged in a fluid communication between the hydrophobic membrane and the gas outlet and/or gas inlet.

In some exemplary embodiments, the device for separating the condensate is, or comprises, a humidity exchanger. A humidity exchanger is preferably a device, which has at least in parts a high permeability for water (steam) while being gas-tight or having a high gas-tightness at the same time. In some embodiments, humidity may be removed by a humidity exchanger from a gas (particularly air) of the blood treatment apparatus or from a gas (particularly air) which is led through the latter or through the extracorporeal blood circuit. In some embodiments, the humidity exchanger is part of a disposable of the blood treatment apparatus. In some embodiments the humidity exchanger comprises Nafion.

In some exemplary embodiments, the device for separating the condensate is, or comprises, a humidity trap, which separates and/or binds condensate by means of a cooling element, e.g. a Peltier element.

In some exemplary embodiments, the blood treatment apparatus is embodied as an acute dialysis apparatus, dialysis apparatus, hemodialysis apparatus, hemofiltration apparatus, apheresis apparatus, plasma treatment or plasma exchange apparatus, TPE (Therapeutic Plasma Exchange) apparatus, and/or combinations thereof.

In some exemplary embodiments, the medical treatment apparatus comprises a control or regulating device which is programmed to execute or prompt some or all of the steps of the method, in particular steps of the de-aeration procedure.

In some exemplary embodiments, the single-needle pneumatic unit comprises the compressor, the condensate collection and a single-needle tank and/or may be equated with an arrangement comprising the aforementioned components.

In some exemplary embodiments, the compressor is directly in fluid communication with the gas outlet of the blood treatment apparatus through a fluid line. "Directly" may signify that only one tube connection is provided without any further components integrated in the fluid path.

In some exemplary embodiments, the single-needle pneumatic unit comprises a condensate evaporator which is connected, in particular directly, in fluid communication to the gas inlet by means of a line.

In some embodiments, the condensate trap contains no filter.

In several embodiments, the condensate trap is designed as one single chamber, i.e. the condensate trap does not comprise e.g. two or more chambers, which are separated, e.g. by a separating wall, and/or connected, e.g. via an opening.

In some embodiments the condensate trap does not comprise a compressed air filter nor a swirl disk and not/nor a sintered filter.

Some or all of the embodiments may encompass one or several advantages mentioned supra or in the following.

The condensate trap allows the condensate water, present, e.g., in the air port of a blood treatment apparatus, to collect. The water may subsequently be conducted away.

Reducing the humidity by separating condensate may, in particular for blood treatment options, in which hydrophobic filters or hydrophobic membranes are used in a gas flow path, prevent wetting the filters or membranes. Hydrophobic filters wetted with liquid are impermeable for gas. In case this takes place during the blood treatment, the blood treatment may have to be stopped.

In some blood treatments, comparatively large amounts of moisture-saturated air are alternately conveyed into a container and conveyed out of it again. The latter process is known from single-needle blood treatments, in which air is conveyed out of a single-needle chamber or a blood cassette through a hydrophobic filter into a pressure tank being on the side of the machine (the single-needle tank) where said air is stored until it gets conveyed again into the blood cassette through the hydrophobic filter. On the way into the pressure tank, the air is guided through pneumatic lines, where it cools down. Moisture condenses, due to temperature differences, in form of drops at the inner side of the pneumatic lines. If the air flows in the next cycle out of the pressure tank back into the single-needle chamber, then said air is optionally compressed by the compressor more or less strongly, which may lead to a moisture supersaturation. The condensate forms finally also at the outlet of the compressor. Once condensate drops are present, they serve as condensation nuclei. They grow until they constrict the pneumatic lines in transverse section until they may be carried away by the air flow.

Since for reasons concerning the treatment efficiency, an increased blood flow, is usually used, in the venous phase, compared to the arterial phase, condensate drops are preferably carried away towards the hydrophobic filter/hydrophobic membrane of the blood cassette. If the condensate reaches the hydrophobic membrane, the latter becoming thus impermeable for air, the treatment must be stopped.

Condensate may thus be largely retained, so that wetting the hydrophobic filter is advantageously avoided.

Some embodiments described herein may be implemented at low cost. The condensate trap described herein is suitable to be retrofitted. It may be hygienically advantageously manufactured as a disposable or single-use article.

Further advantages, in particular of the exemplary embodiments shown in the figures, are described below.

The present invention shall be exemplarily explained with reference to the accompanying drawings in which identical reference numerals denote same or similar components. In the partially strongly simplified figures, the following applies:

DETAILED DESCRIPTION OF THE FIGURES

Figure 1:
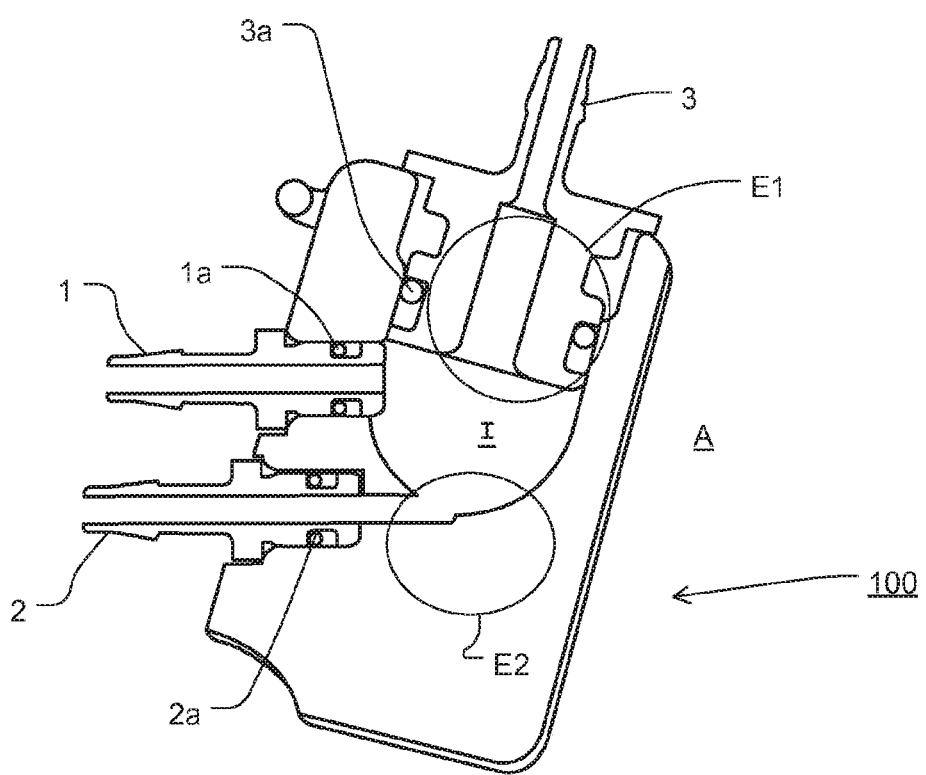
FIG. 1 shows a longitudinal section of a condensate trapof an exemplary embodiment.

FIG. 1 shows a longitudinal section of a condensate trap 100 according to an exemplary embodiment of the present invention.

The condensate trap 100 comprises an interior I which may be understood as a compartment or chamber suitable for receiving or conducting. The interior I may to this end, as shown in FIG. 1, be sealed against an exterior A of the condensate trap 100 so that a gas exchange between the interior I and the exterior A of the condensate trap 100 is only possible through ports of the condensate trap 100.

Figure 3:
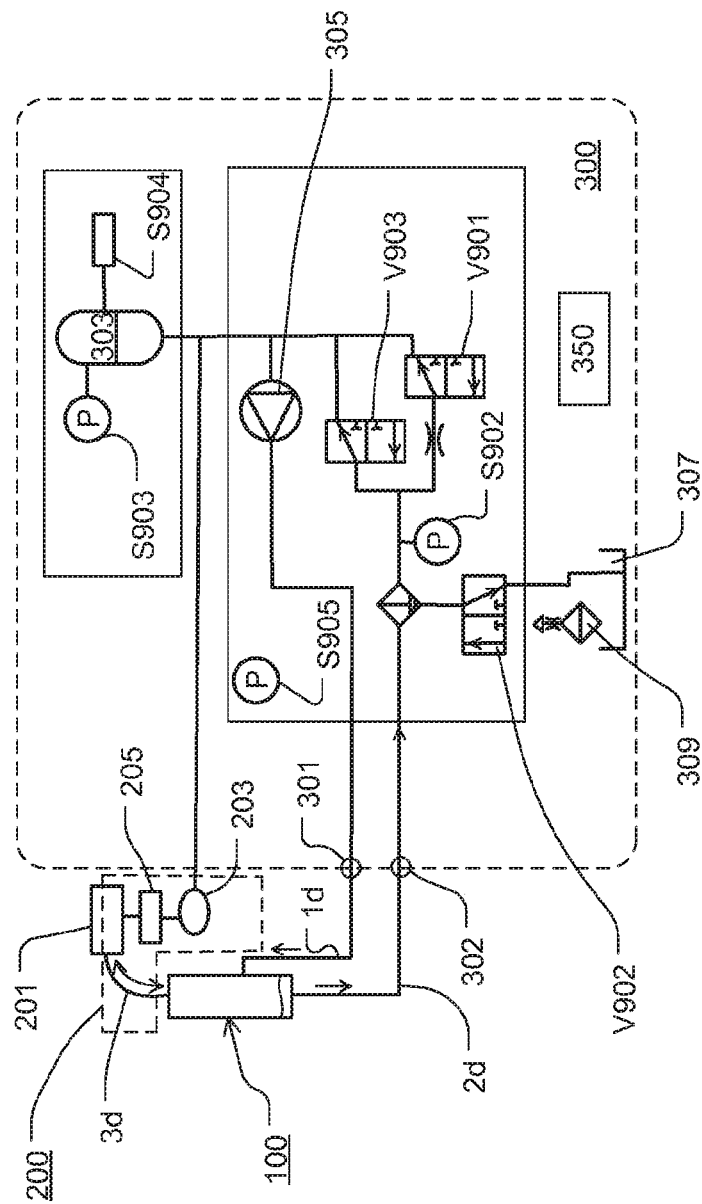
FIG. 3 shows a schematically simplified portions of a single-needle pneumatic unit of a blood treatment apparatus.

The ports comprised by the condensate trap 100 for this purpose are: a first port 1 for—e.g. directly or indirectly (i.e. for example via tubes)—connecting the interior I in fluid communication with a gas outlet 301, being illustrated only in FIG. 3, of a blood treatment apparatus 300, a second port 2 for connecting the interior I in fluid communication with a gas inlet 302, being illustrated only in FIG. 3, of the blood treatment apparatus 300 and a third port 3 for connecting the interior I to a gas inlet/gas outlet, e.g. to an air port or compressed air port 201—again being illustrated only in FIG. 3—of e.g. a blood tubing set or of a blood cassette 200, see FIG. 3.

A sealing between interior I and exterior A may be achieved by O-rings 1a, 2a and 3a or in a different manner.

The ports 1, 2 and/or 3 may, as exemplarily seen in FIG. 1, be embodied as female or male end pieces of connectors. They may be embodied as parts of Luer connectors. They may comprise bayonet-connector elements. They may be provided or used for the connection or for connecting to tubes.

The condensate trap 100 may in each embodiment be optionally made of POM (Polyoxymetheylene) or may comprise POM. Spouts of the condensate trap 100 may be passivated, e.g. by a metal or aluminum or may be covered or coated with these materials or another corrosion protection.

Figure 2:
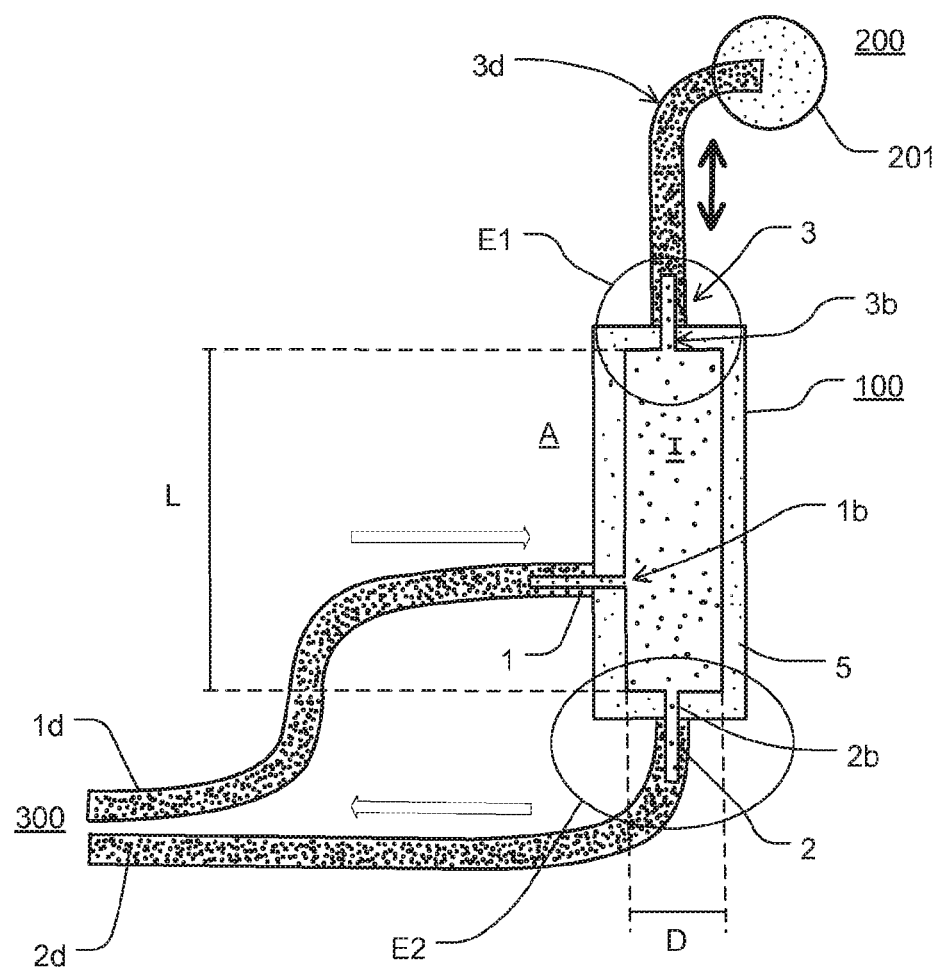
FIG. 2 shows a longitudinal section of a condensate trap in a second exemplary embodiment.

FIG. 2 shows a longitudinal section of a condensate trap 100 in a second exemplary embodiment. Its interior I has an extension D in a transverse direction and an extension L in longitudinal direction. E1 and E2 denote in FIG. 2 the first or second end area.

The interior I is separated from the exterior A by a housing 5. The housing 5 comprises a first opening 1b, a second opening 2b and a third opening 3b. They serve the gas exchange between the interior I and the gas inlets and gas outlets 301, 302, and 201 which are connected to the condensate trap 100.

In the exemplary embodiment shown in FIG. 2, the distance between the first opening 1b and the third opening 3b is at least as big as the extension D of the interior I in its transverse direction, for example its inner diameter. The inner diameter may be e.g. within a range from 1 mm to 4 mm, preferably it is between 1.2 mm or 2.0 mm, or an arbitrary intermediate value.

In the exemplary embodiment shown in FIG. 2, the distance between the first opening 1b and the second opening 2b is optionally as big as the extension D of the interior I.

In FIG. 2, the first port 1 is connected to a connection tube 1d, which is provided to connect in fluid communication the interior I to the gas outlet 301, shown in FIG. 3, of a blood treatment apparatus 300 being only roughly indicated in FIG. 2.

In FIG. 2, the second port 2 is connected to a connection tube 2d which is provided to connect in fluid communication the interior I to the gas inlet 302, shown in FIG. 3, of a blood treatment apparatus 300 being only roughly indicated in FIG. 2.

In FIG. 2, the third port 3 is connected to a connection tube 3d which is provided to connect in fluid communication the interior I to a compressed air port or air port 201, shown in FIG. 3, of a blood cassette 200 being only roughly indicated in FIG. 2, wherein the air port 201 serves as gas inlet and/or gas outlet of the blood cassette 200. The connection tube 3d is embodied as short as possible, e.g. 1 cm to 6 cm, e.g. between 2 cm and 5 cm, or it has an arbitrary intermediate value.

FIG. 1 and FIG. 2 show the condensate trap 100 in a use position, i.e. in a perpendicular position or substantially perpendicular position, in which a first end area E1 of the condensate trap 100 or of the interior I is arranged further to the top than a second end area E2, lying opposite to first end area E1, of the condensate trap 100 or of the interior I.

The arrows illustrated next to the connection lines 1d, 2d, and 3d indicate the flow direction of the gas when the condensate trap 100 is in operation.

FIG. 3 shows schematically simplified portions of a single-needle pneumatic unit of a blood treatment apparatus 300. Although FIG. 3 indicates a relation of the present invention to a single-needle treatment, the present invention is not limited thereto. Some embodiments are suitable for use in each extracorporeal blood treatment in which moisture-saturated air (or in general: gas) is alternately conveyed back and forth, and in which one expects benefits of removing moisture or condensate.

The single-needle pneumatic unit of FIG. 3 comprises, optionally, a single-needle tank 303. The latter serves to intermediately store gas from a single-needle chamber 203 of a blood treatment cassette 200 being only roughly indicated in FIG. 3. Its capacity may reach around 300 ml.

A pressure sensor S903 and/or a temperature sensor S904 may be optionally provided for measuring pressure or temperature of the gas stored in the single-needle tank 303.

Further pressure sensors S902 and S905 may be provided upstream or downstream of a compressor 305 of the single-needle pneumatic unit. A bypass line and valves V901 and/or V903 for releasing or activating it may further be provided.

The single-needle pneumatic unit shown in FIG. 3 comprises a gas outlet 301 arranged downstream of the compressor 305 and a gas inlet 302 arranged upstream of the compressor 305 and/or of the single-needle tank 303. They are in FIG. 3 connected to the connection lines 1d or 2d, respectively.

As is seen in FIG. 3, the blood cassette 200 is supplied with air, after the latter—being effected by the compressor 305—perfuses the condensate trap 100. The air is supplied directly by the compressor 305 in FIG. 3. Therein, the air flows through the port 1 (which is positioned higher during use of the condensate trap 100), into the interior I of the condensate trap 100, and from there further towards the air port 201.

The situation can be different with the exhaust air of the air port 201, i.e. the air extracted out of the blood cassette 200 through the air port 201. Said air perfuses the second port 2 positioned lower—when compared to the first port 1—into the gas inlet 302 of the single-needle pneumatic unit. The wet part of the exhaust air is separated, directly after the gas inlet 302, from the fluid flow and conveyed to an optional condensate collection 307. The condensate collection 307 may be connected to a device for evaporating and/or to an aeration or deaeration device 309.

Figure 4:
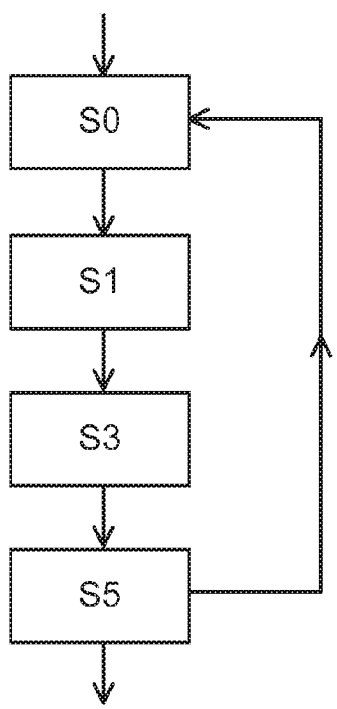
FIG. 4 shows a schematically simplified execution of the method in an exemplary embodiment.

FIG. 4 shows schematically simplified the execution of the method according to the present disclosure in an exemplary embodiment.

The method encompasses providing a blood treatment apparatus according to the present disclosure which comprises a blood pump in addition to the compressor 305.

The blood treatment apparatus 300 is being, or is connected to a blood cassette 200, which comprises a single-needle chamber 203 and an air port 201. The blood cassette 200 further comprises a hydrophobic membrane 205 which is arranged in fluid communication between the single-needle chamber 203 and the air port 201.

The blood treatment apparatus 300 comprises a control device 350 which is schematically shown in FIG. 3 and which is programmed to execute or effect at least once a ventilation process comprising or consisting of the following steps:

In an optional step S1, a pre-determined pressure is built up in the single-needle chamber 203. This may be achieved by means of the blood pump and/or by means of the compressor 305. If the building up of pressure is achieved by the compressor, then this is preferably done at a conveying rate, which does not exceed the conveying rate at which air is conveyed into the single-needle chamber 203 in the venous phase, i.e. when emptying the single-needle chamber 203.

In step S3 the pressure is released towards the single-needle tank 303 or in the surroundings in order to achieve a high-peak flow. This may take place abruptly by opening a valve.

In step S5, again optional, conveying takes place with an open valve V903 between condensate collection and compressor inlet by means of the compressor 305. This serves conveying the condensate into the single-needle pneumatic unit. There, it may be separated by a special arrangement (e.g. a collection chamber with a facility for emptying the lowest point of the single-needle pneumatic unit).

The control device 350 may be programmed to execute the de-aeration procedure with the steps S1 to S5 whenever a pre-determined condition has been fulfilled. The possible pre-determined conditions may include the completion of a pre-determined period of time since the de-aeration executed last, reaching/falling below a pre-determined temperature, reaching/falling below a pre-determined flow ratio and/or detecting a pre-determined wavelength, e.g. in transmission or light scattering measurements at the gas inlet 302. The presence of the pre-determined condition may be checked in a higher-level step S0.

LIST OF REFERENCE NUMERALS 100 condensate trap
1 first port
1a O-ring
1b opening in the housing
1d connection line
2 second port
2a O-ring
2b opening in the housing
2d connecting line
3 third port
3a O-ring
3b opening in the housing
3d connection line
5 housing
A exterior
D extension in transverse direction E1 first end area
E2 second end area
I interior
L extension in longitudinal direction
200 blood cassette
201 air port, compressed air port
203 single-needle chamber
205 hydrophobic membrane; hydrophobic filter
300 blood treatment apparatus
301 gas outlet
302 gas inlet
303 single-needle tank
305 compressor
307 condensate collection
309 aeration or de-aeration device
350 control device
S902 sensor
S903 sensor
S904 sensor
S905 sensor
V901 valve
V903 valve

The invention claimed is:

1. A medical condensate trap for use in a blood treatment performed externally using a blood treatment apparatus, wherein the condensate trap comprises:
   an interior;
   a first connector structured to connect with tubing and defining a first port on a first surface of a housing of the condensate trap, wherein the first port is fluidly coupled with the interior, and wherein the first connector is configured to connect the interior to a gas outlet of the blood treatment apparatus in fluid communication;
   a second connector structured to connect with tubing and defining a second port on a second surface of the housing, wherein the second port is fluidly coupled with the interior, wherein the second connector is configured to connect the interior to a gas inlet of the blood treatment apparatus in fluid communication; and
   a third connector structured to connect with tubing and defining a third port on a third surface of the housing, wherein the third port is fluidly coupled with the interior, wherein the third connector is configured to connect the interior to an air port of a blood treatment device;
   wherein:
      the condensate trap is configured to dehumidify at least one section of the blood treatment apparatus or the blood treatment device without the use of a filter;
      the second surface of the housing and the third surface of the housing are spaced apart and are parallel to each other; and
      and the first surface extends between the second surface of the housing and the third surface of the housing and is generally perpendicular to the second surface of the housing and the third surface of the housing.

2. The medical condensate trap according to claim 1, wherein the condensate trap is configured to be used in an orientation in which the third port is arranged higher than the first port and the second port.

3. The medical condensate trap according to claim 1, wherein the condensate trap is configured to be used in an orientation in which the third port is arranged higher than the first port or the second port.

4. The medical condensate trap according to claim 1, wherein the condensate trap is configured to be used in an orientation in which the first port is arranged higher than the second port.

5. The medical condensate trap according to claim 1, wherein the third port is associated with a first end area of the interior, wherein the second port is associated with a second end area of the interior, wherein the second end area is opposite to the first end area, and wherein the first port is arranged between the second port and the third port.

6. The medical condensate trap according to claim 1, wherein the interior is separated by the housing from an exterior of the condensate trap, wherein the interior has an extension in a longitudinal direction and an extension in a transverse direction, and wherein the housing comprises:
   at least a first opening fluidly connected with the interior through the first port;
   at least a second opening fluidly connected with the interior through the second port; and
   at least a third opening fluidly connected with the interior through the third port.

7. The medical condensate trap according to claim 6, wherein the distance between the first opening and the third opening is greater than or equal to the extension in the transverse direction.

8. The medical condensate trap according to claim 6, wherein the distance between the first opening and the second opening is greater than or equal to the extension of the interior in the transverse direction.

9. The medical condensate trap according to claim 6, wherein tubes, with an inner diameter, are connected to the first, second, and third ports, and wherein the inner diameter is less than the extension of the interior in the transverse direction.

10. The medical condensate trap according to claim 6, wherein a diameter, a surface, or a length of a surface of at least one of the first opening, the second opening, or the third opening, is smaller than the extension of the interior in the transverse direction.

11. The medical condensate trap according to claim 1, wherein the blood treatment device comprises a blood tubing set or a blood cassette.

12. A blood treatment apparatus which comprises, or is connected to, a condensate trap, wherein the condensate trap comprises:
   an interior;
   a first connector structured to connect with tubing and defining a first port that is fluidly coupled with the interior, wherein the first connector is fluidly coupled to a gas outlet of the blood treatment apparatus;
   a second connector structured to connect with tubing and defining a second port that is fluidly coupled with the interior, wherein the second connector is fluidly coupled to a gas inlet of the blood treatment apparatus; and
   a third connector structured to connect with tubing and defining a third port that is fluidly coupled with the interior, wherein the third connector is fluidly coupled to an air port of a blood cassette or blood tubing of a blood treatment device;
   wherein the condensate trap is configured to dehumidify at least one section of the blood treatment apparatus or the blood treatment device without the use of a filter.

13. The blood treatment apparatus according to claim 12, wherein the blood treatment apparatus is embodied as a blood tubing set and a blood cassette.

* * * * *